US009658206B2

(12) United States Patent
Siwy et al.

(10) Patent No.: US 9,658,206 B2
(45) Date of Patent: May 23, 2017

(54) FASTER RESISTIVE-PULSE SENSING TOGETHER WITH PHYSICAL AND MECHANICAL CHARACTERIZATION OF PARTICLES AND CELLS

(71) Applicant: The Regents of the University of California, Oakland, CA (US)

(72) Inventors: Zuzanna S. Siwy, Irvine, CA (US);
Kenneth J. Shea, Irvine, CA (US);
Ken Healy, Auburn, AL (US); Laura Michele Innes, Cerritos, CA (US);
Matthew Schiel, Irvine, CA (US);
Matthew Pevarnik, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 423 days.

(21) Appl. No.: 14/274,404

(22) Filed: May 9, 2014

(65) Prior Publication Data
US 2014/0332381 A1    Nov. 13, 2014

Related U.S. Application Data

(60) Provisional application No. 61/821,379, filed on May 9, 2013.

(51) Int. Cl.
| G01N 27/447 | (2006.01) |
| G01N 33/487 | (2006.01) |
| G01N 15/12  | (2006.01) |

(52) U.S. Cl.
CPC ... *G01N 33/48721* (2013.01); *G01N 15/1218* (2013.01); *G01N 27/44791* (2013.01)

(58) Field of Classification Search
CPC .......... G01N 27/3275; G01N 27/3276; G01N 27/3278; G01N 15/12; G01N 15/1209; G01N 15/1218; G01N 15/1236
See application file for complete search history.

(56) References Cited

U.S. PATENT DOCUMENTS

| 4,778,657 A * | 10/1988 | Spohr ................ G01N 15/1218 324/71.4 |
| 7,851,203 B2 * | 12/2010 | Letant .................. B01D 67/006 204/403.06 |

FOREIGN PATENT DOCUMENTS

CN     102590314 A  *  7/2012   ........... G01N 27/403

OTHER PUBLICATIONS

Cambridge Dictionary definition of "undulate" downloaded from Cambridge Dictionary definition of "undulate" on Aug. 12, 2016.*
(Continued)

*Primary Examiner* — Alexander Noguerola
(74) *Attorney, Agent, or Firm* — Marcus C. Dawes; Daniel L. Dawes

(57) ABSTRACT

A method for multiplex characterization of individual particles by their size, shape, mechanical properties (deformability), and chemical affinity to recognition agents. The analysis can be performed from concentrated solutions. The method detects transient sticking of particles in the pore and points to its location along a pore axis. If a pore is decorated with a recognition agent for an analyte present in a solution, it is possible to distinguish specific binding at the place of the recognition agent, and non-specific adsorption of the analyte. The method confirms whether any individual particle or hydrogel completely translocates the pore and allows unambiguous detection and characterization of multiple particles or hydrogels in the pore, which would previously corrupt the results, so that higher analyte concentrations can be used for faster analysis. High aspect ratio of the pores (ratio of pore length and diameter) together with the pattern of ion current pulses also allow passage of the same particle or cell multiple times without letting the cell exit the pore.

22 Claims, 14 Drawing Sheets

(56) References Cited

OTHER PUBLICATIONS

Adamo et al., "Microfluidic-based assessment of cell deformability," Anal. Chem. Aug. 7. 2012; 84(15); 6438-6443.*
Javanmard et al., "Pulse Width Modulation Using Coded Corrugated Micro-Fluidic Sidewalls for Low Signal-Noise Ratio Single Cell Impedance Cytometry," 15th International Conference on Miniaturized Systems for Chemistry and Life Sciences Oct. 2-6, 2011, Seattle, Washington, USA, pp. 1998-2000.*
Bator et al., "Erythrocyte Deformability and Size Measured in a Multiparameter System That Includes Impedance Sizing," Cytometry 5:34-41 (1984).*
EPO computer-generated English language translation of Lu et al. CN 102590314 A, patent published Jul. 18, 2012.*
Luan et al., "Control and reversal the electrophoretic force on DNA in a charged nanoopre," J. Phys. Condens. Matter 22 (2010) 454123 (5 pp).*

\* cited by examiner

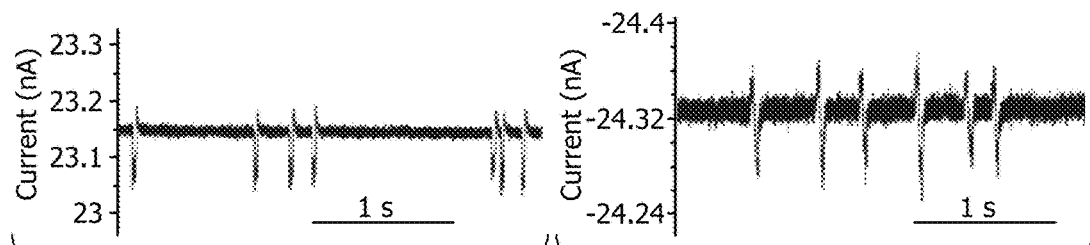
FIG. 9A
FIG. 9B
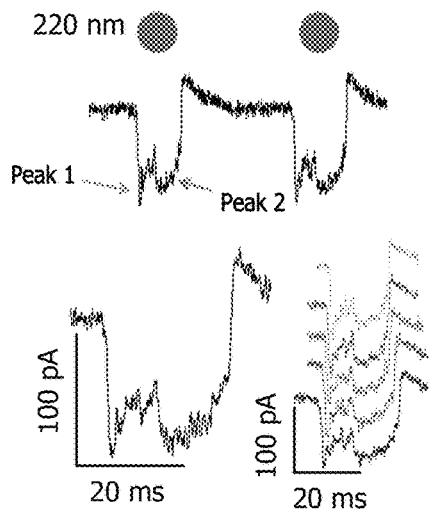
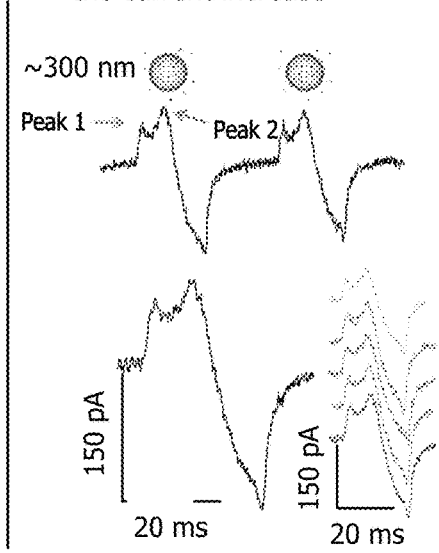
FIG. 10

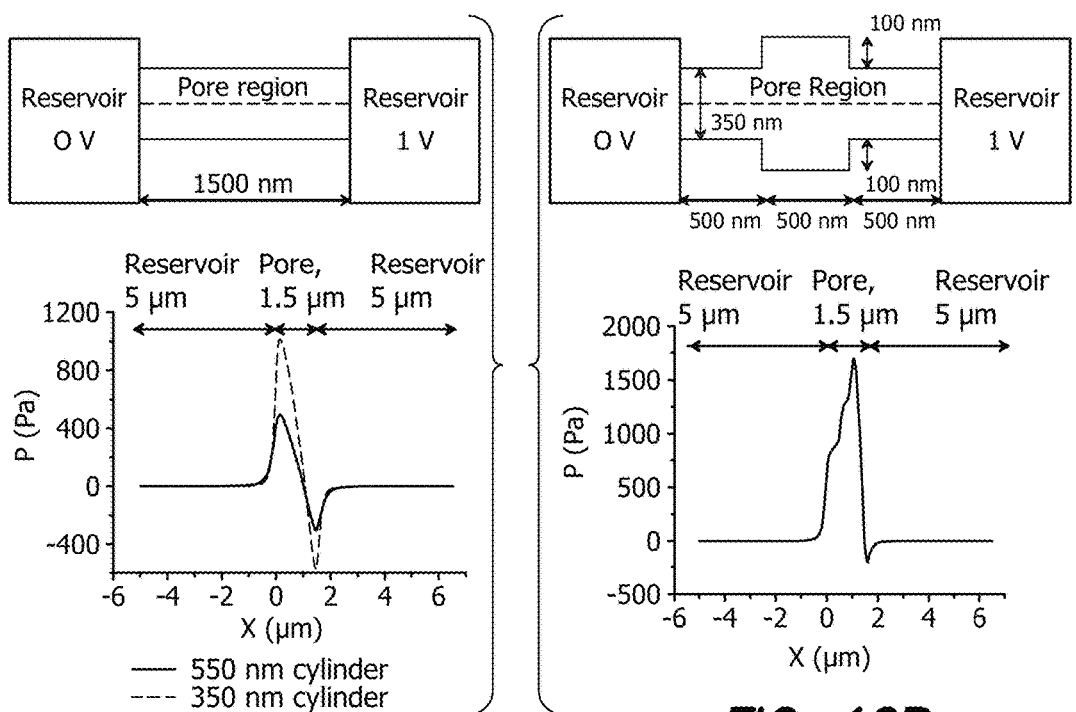
FIG. 12A
FIG. 12B
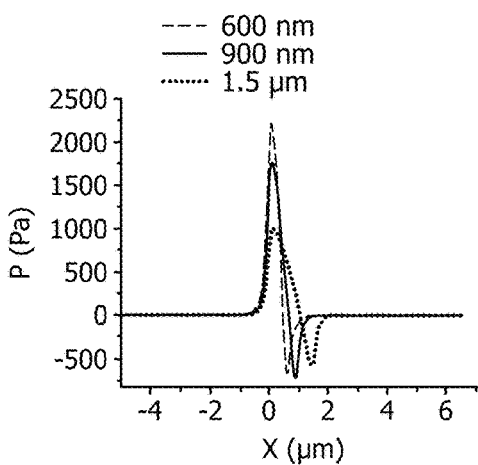
FIG. 13A
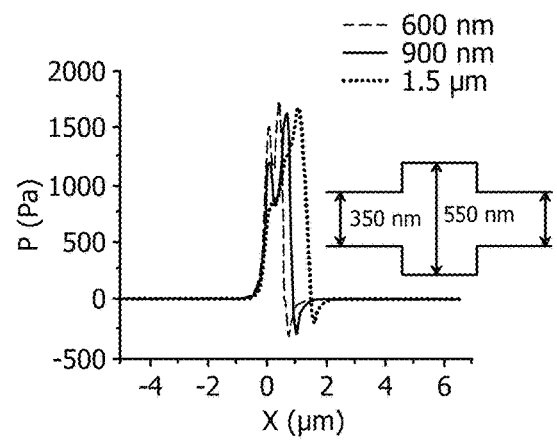
FIG. 13B

Escherichia Coli

Staphylococcus Aureus

FASTER RESISTIVE-PULSE SENSING TOGETHER WITH PHYSICAL AND MECHANICAL CHARACTERIZATION OF PARTICLES AND CELLS

RELATED APPLICATIONS

The present application is related to U.S. Provisional Patent Application Ser. No. 61/821,379, filed on May 9, 2013, which is incorporated herein by reference and to which priority is claimed pursuant to 35 USC 120.

GOVERNMENT RIGHTS

This invention was made with government support under CHE0747237 awarded by the National Science Foundation. The government has certain rights in the invention.

BACKGROUND

Field of the Technology

The disclosure relates to the field of resistive pulse sensing, specifically to a process and method for analyzing the size, charge, shape, mechanical and other properties of micro- and nano-sized particles, including biological cells and viruses.

Description of the Prior Art

Resistive-pulse sensing involves the detection and analysis of particles as they pass through a channel or pore separating two reservoirs of electrolyte solution. The resistance of that pore is monitored by applying a voltage between the reservoirs, which drives a flux of ions through it, detected as a current flowing from the voltage source. Particles may be driven through the pore electrokinetically thus by electroosmosis and/or electrophoresis, by pressure, or simply move by diffusion, and they modulate the flux of ions as they pass through, thus inducing pulses in the measured resistance. In addition to counting particles, analysis of these pulses allows estimation of particle size, electrophoreticmobility, effective charge, and measurement of the size and volume of the pore used to analyze those particles.

Single-pore technology has been used to detect particles and determine their size. The approach works well for objects of very different sizes. Single nanopores with diameters less than 10 nm are used to detect single molecules such as DNA and proteins. Pores with openings of several tens and several hundreds of nanometers were shown to detect viral capsids and particles. Pores of micrometer size are routinely used in complete blood counts at hospitals. In all the above-mentioned cases, the species to be detected were in contact with one side of a single-pore membrane that separated two chambers of a conductivity cell filled with an electrolyte. Single molecules, particles, and cells were detected during their passage through the pore as a transient change in the recorded ion current called the resistive pulse.

Passing of particles through pores is also very important in the context of drug delivery, when considering particle clearance from the body. Hydrogels have become the center of interest since it was shown that by applying a pressure difference these deformable particles could pass through pores whose diameters were much smaller than the effective particle size. If used as drug-delivery vehicles, these particles could therefore be cleared through the kidney system, which is known to contain nanopores with effective opening diameters of approximately 8 nm. Clearing particles through the renal system is preferred since it prevents particle accumulation in the liver, which would otherwise lead to hepatoxicity. Transport experiments of 116 nm diameter hydrogels were performed with polymer membranes containing multiple pores with an average opening of 10 nm.

Detecting deformable particles with single pores could potentially provide more information than measurements with many-pore membranes. By studying resistive pulses one could learn about the dynamics of the particle deformation on a single-particle basis. Since multi-pore membranes contain pores with a finite distribution of the pore diameters, having one pore of known geometry allows one to understand the relation between the pore opening diameter and the pressure required for the particle deformation. Studies with single man-made pores and hydrogels have been performed under an applied pressure difference using glass pipettes, with openings between 200 and 700 nm, and 570 nm diameter hydrogel particles. Transport of single hydrogels led to the formation of a unique pattern of the resistive pulses consisting of a current increase followed by a current drop below the baseline value. Since the particles were largely filled with salt solution and additionally carried surface charges, their approach to the pore opening resulted in the increase of the measured transmembrane current. In order to squeeze through an opening that was smaller than the particle size, the particles had to deform and dehydrate, which was observed as a current decrease. The pulse shape was found to be dependent on the value of the applied pressure difference and the pore diameter. If the particles passed through sufficiently wide pipettes, the pulse consisted of only one positive peak, indicating that the presence of the particle in the pore lowered the system resistance. It is important to mention that in this system deformation of particles could be observed only in cases when the particles were passing through pipettes with openings smaller than the particles' diameter.

The use of single nanopores in detecting particles and biological cells is known and has been documented. See for example U.S. Pat. No. 2,656,508, DeBlois, R. W., Bean, C. P.; Wesley, R. K. A. "Electrokinetic Measurements with Submicron Particles and Pores by the Resistive Pulse Technique," *J. Colloid Interface Sci.* 1977, 61, 323-335; and DeBlois, R. W.; Bean, C. P. "Counting and Sizing of Submicron Particles by the Resistive Pulse Technique," *Rev. Sci. Instrum.* 1970, 41, 909-916.

The first example of resistive-pulse sensing was the Coulter counter developed to count and size blood cells. The Coulter counter has since been used to characterize a variety of analytes, including bacteria, mitochondria, viruses and gas bubbles. With the advent of track-etched pores, resistive pulse sensing was extended to counting and sizing nanoscale particles, such as polystyrene spheres and viruses. Later, ion channels enabled sensing of polymers and small molecules as well as of nucleic acids and proteins and are now on the cusp of sequencing DNA. Recently, resistive-pulse sensing has been demonstrated with solid-state nanopores, silica nanochannels, gold nanoconstriction, and PDMS nanochannels. The central part of the Coulter counter device comprises a single pore which gets transiently occluded when single particles (e.g. biological cells) pass through under the influence of an applied pressure difference and electric field.

The commercial unit of the Beckman Coulter counter is applicable for the detection and counting of blood cells. The detection is based on the difference in volume of various cells. The technique used by the commercial Beckman Coulter is thus not capable of detecting cells of different shapes. The commercially available unit does not characterize mechanical properties of any transport objects and cannot perform any affinity studies, e.g. distinguishing cells based on their ability to bind to specific agents. Flow cytometry is a more versatile device allowing studies of cells and particles' chemical affinity, size and even sub-cellular structures but often requires staining of the cells, which compromises their viability. There is currently no tool on the market capable of high-throughput characterization of mechanical properties of cells and particles. None of the tools offer a possibility of simultaneous characterization of size, shape, mechanical properties and chemical affinities on a single object level.

In addition, the commercial unit cannot be used to detect circulating tumor cells (CTCs), which are shed from a tumor site into the blood stream. CTCs are extremely rare (a few or a few tens of cells per 10 mL of blood) and thus cannot be detected within the large background of the blood cells. Moreover, the Beckman Coulter counter requires even further dilution of the blood samples. There has been a lot of interest in detecting and analyzing CTCs since their presence is related with malignancy of tumors and their response to therapy. CTCs also give insight into the heterogeneity of cancer cells. If a sufficient number of CTCs were isolated, various anticancer drugs could be tested to design personal and more efficient treatment for each patient.

It was noted in the past that electrical fluctuations within a resistive pulse correspond to physical variations in the structure of the pore. However, this has seen little application, used only to determine the base and tip diameters of a conical pore and to reveal the tapered shape of glass nanopipettes. In addition, although surfactant is routinely added to the particle solution to prevent aggregation and mitigate pore clogging, the significant impact of surfactant on particle velocity has never been reported.

Microfluidic channels have been successfully applied to detect CTCs. Some of the existing microfluidic devices are based on the volume of CTCs which is often larger compared to the volume of red and white blood cells; other devices combine the size and deformability of CTCs, for example as disclosed by W. Zhang, K. Kai, D. S. Choi, T. Iwamoto, Y. H. Nguyen, H. Wong, M. D. Landis, N. T. Ueno, J. Chang, L. Qin, *Proc. Natl. Acad. Sci. U.S.A.* 2012, 109(46), 18707-18712; S. C. Hur, N. K. Henderson-MacLennan, E. R. B. McCabe, D. Di Carlo, *Lab Chip* 2011, 11(5), 912-920; review: I. Cima, C. W. Yee, F. S. Iliescu, W. M. Phyo, K. H., Lim, C. Iliescu, M. H. Tan. *Biomicrofluidics* 2013, 7, 011810 (1-17)]. Another microfluidic system to characterize CTCs by their size and mass as well as deformability has been reported by Byun et al. in *Proc. Natl. Acad. Sci. USA* doi: 10.1073/pnas.1218806110 (2013). These approaches require the cells to pass through constrictions significantly smaller than the cells, which can compromise the cells' viability.

The only FDA approved system for detecting CTCs (CellSearch, Veridex, LLC) uses the presence of Epithelial Cell Adhesion Molecule (EpCAM) on the cell surface and the binding of cells to an antibody towards EpCAM. However, since not all CTCs over express EpCAM, this method is not capable of detecting all CTCs and cells originating from different primary tumors.

The current resistive pulse technique used in the art is performed from diluted solutions, which slows down the analysis. In addition, prior art methods cannot distinguish between particles of different shapes, but only similar volume and charge. Detecting shape is relevant for the detection of viruses and cells, since misshapen cells can be indicative of disease. Current resistive-pulse techniques also cannot characterize cells by their mechanical properties, and cannot be applied for the detection of circulating tumor cells (CTC).

What is needed is a device and method that involves using single pores with varying cross-sectional sizes and pore roughness that leads to repeatable signatures of ion current being recorded when the particles are translocating the pore. A platform is needed which is capable of increasing the throughput of the Coulter counter approach by at least an order of magnitude with less or no dilution.

The needed platform should be able to simultaneously characterize each individual cell with multiple physical properties including size, shape, surface charge and deformability. Characterization of the physical properties together with characterization of chemical affinities is important as well.

BRIEF SUMMARY

The current invention performs resistive-pulse sensing in long cylindrical pores with undulating diameters. Specifically, as particles pass through these pores, they consistently give resistive pulses with a repeatable pattern of variations. This pattern gives several advantages and contains several unique capabilities as compared to typical resistive-pulse sensing. The patterns may also be used to detect transient sticking of particles to the pore, and confirm whether any individual particle completely translocates (i.e. passes through) the pore. The pattern also enables unambiguous detection of multiple particles within the pore. Using current resistive-pulse sensors, multiple particles in the pore would typically corrupt the results, so the analyte concentration must be kept low enough to avoid this situation. Analysis speed is proportional to concentration, so the current invention will allow for higher concentrations and thus faster analysis. Additionally, these resistive-pulse variations due to the pore structure enable differentiation between particles of the same volume and charge, but with different shapes. This process in not possible using today's resistive-pulse sensors. The undulating pore diameter of the pores leads to hydrodynamic fluid flow with inhomogeneous pressure distribution along the pore axis which can be used to probe mechanical properties of the transported objects, on a single particle or cell basis. It has also been found that the concentration of surfactant used has a significant effect on the particle translocation velocity. This notion has not been found in the prior art, and could be potentially useful for optimizing the sensor for different analytes.

The current invention uses resistive pulse sensing of polystyrene spheres passing through track-etched polyethyleneterephthalate (PET) pores. Our results show that the diameter of these pores fluctuates repeatedly along their length, which we analyze by studying the corresponding variations in the measured resistive pulses. We demonstrate that this repeatable pattern of variations in the ion current signal allows unambiguous resolution of multiple particles in the pore at once and detection of particles transiently sticking in the pore. Compared to classical Coulter counter systems, resistive-pulse sensing using pores with varying cross-section can thus be performed at higher analyte concentrations, since multiple events can be easily resolved. We also believe that particles of the same size and charge, but different shapes, will modulate these resistive-pulse signals in distinct ways due to the varying pore cross-section, thus allowing differentiation between them.

The pores with an undulating opening diameter will be able to characterize particles and cells by shape, size, and mechanical properties e.g. ability to deform. In addition, if the pores are modified with a recognition agent towards a specific molecule present on the surface of particles or cells, screening for the presence of these cells/particles can be performed as well. For example, pores whose one entrance is modified with an antibody towards a protein EpCAM known to be present on the surface of some cancer cells will allow detecting the EpCAM positive cells. Binding of the transported cells to the modified region of the pore will be temporary. Release of a bound cell will be achieved by a spike of pressure or voltage. The current invention will offer the most complete analysis of particles of any type including tumor cells, performed on the single particle/cell basis. The examined objects will not be destroyed during the detection and they will remain viable for further biochemical and biological characterization. The possibility of addressing single cells is especially important after the newest discoveries of the larger inhomogeneity in cells within one primary tumor.

Nanopores in the kidneys are known to carry negative surface charges; thus it would also be of great interest to examine the effect of electrokinetic phenomenon the transport of deformable particles through pores. The current invention demonstrates that passage of hydrogel particles through pores with negative surface charges can indeed occur due to electroosmosis, without an additional pressure difference applied. Since the proposed pores have undulating opening diameter, velocity of the solution flow (e.g. electroosmotic) will be a function of both radial and axial positions, leading to the formation of local pressure differences in the pore. Our measurements were performed with approximately 300 nm diameter hydrogel particles and track-etched pores in polyethylene terephthalate (PET) with opening diameters between 200 and 1600 nm. In all examined pores the recorded resistive pulses consisted of two distinct parts, one above and the other one below the baseline current, suggesting that the particles when in a pore underwent pressure-induced deformation/dehydration, and/or the ionic concentration in the particle and its proximity decreased below the bulk concentration. This is the first report showing particle dehydration in pores larger than the particle diameter, which is caused by the electric field induced pressure differences instead of externally applied pressure difference. The results were explained by modeling ionic transport and electroosmosis-induced pressure profiles in charged pores using Poisson-Nernst-Planck and Navier-Stokes equations. Our results also point to the possibility of formation of a depletion zone in the vicinity of charged particles caused by concentration polarization, which dominates ionic transport through the pores.

The experiments were performed with polymer (PET) pores whose diameter is known to undulate along the pore axis. Consequently, each pore produces a characteristic shape of resistive pulses that reflects local changes in the pore opening. The resistive pulse shape allowed us therefore to elucidate at which location of the pore the dehydration and deformation of the particles occurred. Analysis of the data was facilitated by comparing the shape of resistive pulses corresponding to translocating hydrogels with the recordings performed in the presence of polystyrene particles, which behaved like hard spheres.

The results are of importance for all studies that involve transport of molecules, particles, and cells through pores with charged walls. This is because the experiments and modeling revealed the existence of anon-homogeneous pressure profile along the pore axis, which might affect the geometry of the detected species. In addition, when studying transport of highly charged molecules and particles, it is also important to consider the influence of concentration polarization on ionic transport.

To the best of our knowledge, the resistive-pulse technique is the only nondestructive method of studying the internal structure of high aspect ratio pores. It has been shown recently that the structure of the pore walls can significantly influence ionic transport through nanopores and for many applications of nanoporous membranes, i.e., capacitors, drug-delivery systems, separations, it is important to quantify the pore geometry and wall structure. The method contained herein is used to predict the internal pore structure from the ion current signal during particle translocation is also applicable to other nanopore and nanofluidic systems. Finally, we show that a 20-fold increase in surfactant concentration leads to an approximately 20-fold decrease in particle velocity, which is potentially of practical importance for optimizing the detection of specific analytes.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIGS. 9A and 9B are graphs of ionic current versus time for a 540 nm diameter pore with a 220 nm diameter pore at +1000 mV and a 300 nm diameter hydrogel −1000 mV traversing the pore, respectively.

FIG. 10 is a comparison of current pulses obtained with spherical and cylindrically shaped particles passing through a 2.3 micrometer in diameter pore in 100 mM KCl, ph 10.

FIGS. 12A and 12B are representations of modeling of the pressure profile in 1.5 micrometer long pores that carry a surface charge of −0.25 $e/nm^2$ for two cylindrically shaped pores with an opening diameter of 350 and 550 nm, and for a pore with an undulated pore diameter between 350 and 550 nm, respectively.

FIGS. 13A and 13B are representations of modeling of the pressure profile along a pore axis of a cylindrically shaped pore and for a pore with an undulating pore diameter, respectively.

Figure 1B:
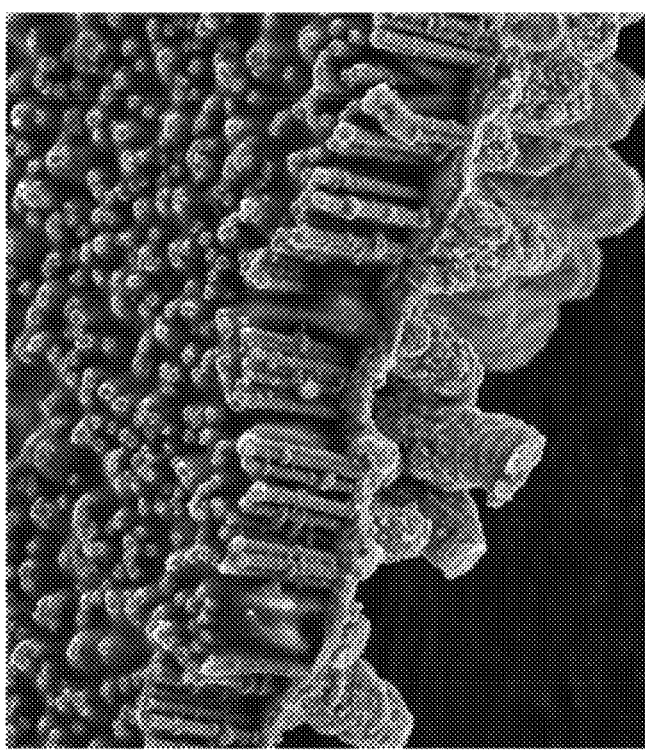
FIGS. 1A and 1B are micrographs of metal replica of pores prepared in polyethylene terephthalate membranes containing $10^8$ pores per $cm^2$.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

The pattern of ion current pulses gives several advantages and unique capabilities compared to typical resistive-pulse sensing. For example, the current scheme can detect transient sticking of particles in pores and in channels. If a pore is decorated with a recognition agent for an analyte present in a solution, it is possible to distinguish specific binding at the place of the recognition agent, and non-specific adsorption of the analyte. It can confirm whether any individual particle completely translocates the pore. It allows unambiguous detection of multiple particles in the pore, which would previously corrupt the results, so that higher analyte concentrations can be used for faster analysis. High aspect ratio of the pores (ratio of pore length and diameter) together with the pattern of ion current pulses also allow passage of the same particle or cell multiple times without letting the cell exit the pore. This is important if only a few cells or particles are present in an analyzed sample and each object has to be analyzed thoroughly. Moving the particle back and forth within the pore is possible by triggered switching on and off of the external voltage that drives the particle transport. The voltage signal is tuned when the particle is in the pore. Previous methods of driving the same particle or cell through the same pore multiple times involved triggering pressure or voltage signal after a particle completely passed through a pore, which led to occasional loss of the particles (e.g. M. Gershow, J. A. Golovchenko. *Nature Nanotech* 2, 775-779 (2007). Switching the voltage off when the particle/cell is passing through a pore leads to immobilization of the object in the pore for a prolonged period of time due to hindered diffusion in a confined geometry.

In addition, the resistive-pulse variations due to the pore structure enable differentiation between particles of the same volume and charge, but with different shapes. Undulating pore diameter of the pores leads to non-homogenous pressure distribution along the pore axis, which can be used as a probe of mechanical properties of passing particles and cells.

Additionally, the current invention can analyze particles at higher concentration, and thus perform a faster analysis, including particle shape. It enables study of the interaction of particles with the pore surface. If a particle sticks in the pore, it is evident where the particle gets stuck, and for how long it is stuck there. Furthermore, it can characterize mechanical properties of particles and cells.

All above mentioned properties can be detected simultaneously on a single particle/cell level. No chemical modification of the cells is necessary thus the cells remain viable. Pores with a varying diameter profile could be incorporated into existing Beckman Coulter Counter systems with minimal modification using the disclosed method. It should also be explicitly understood that microchannels or pores made by means known in the art other than those explicitly described herein can be used when performing the current method without departing from the original spirit and scope of the invention. The accompanying data analysis software would require some updates to exploit the additional information provided by the varying diameter profile. The pores with undulating diameter could be prepared in any material, could also be fabricated as microfluidic channels.

The invention will be applicable for a complete characterization of particles and cells and applied in particular for the detection and characterization of CTCs.

Figure 1A:
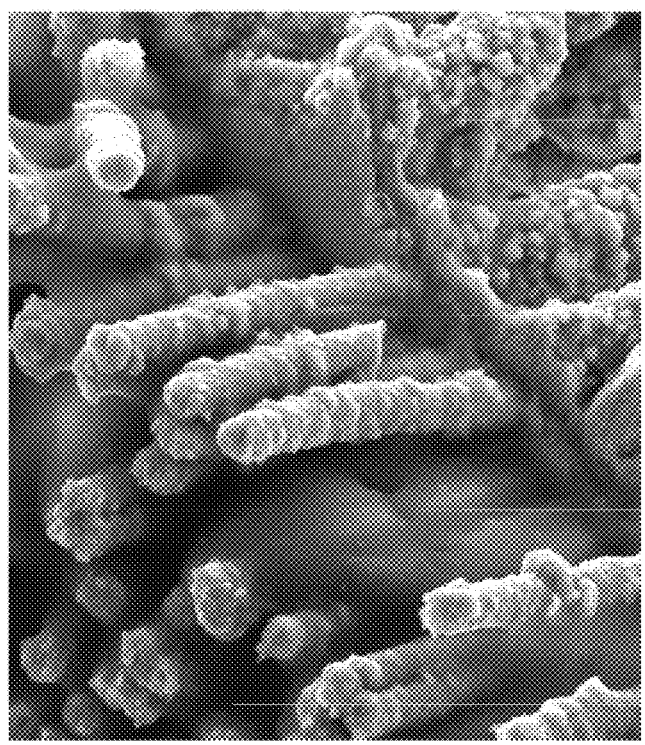

Single pores in polyethylene terephthalate (PET) were used for collecting the experimental results. Known microfluidic devices could equivalently be used for collecting experimental results without significant alteration. The pores were obtained by irradiating 12 micrometer thick films with single energetic heavy ions and subsequent etching in 0.5 M NaOH at 70° C. In order to get information about the roughness of the pore walls, copper replica of pores were prepared and imaged with scanning electron microscopy. To facilitate the imaging, membranes containing $10^8$ pores/cm$^2$ were used for preparing the metal wires. Obtained metal wires confirmed a significant roughness of the pore walls as seen in FIGS. 1A and 1B. The same technique can be used to prepare longer pores needed for the detection of larger objects such as biological cells.

Figure 2A:
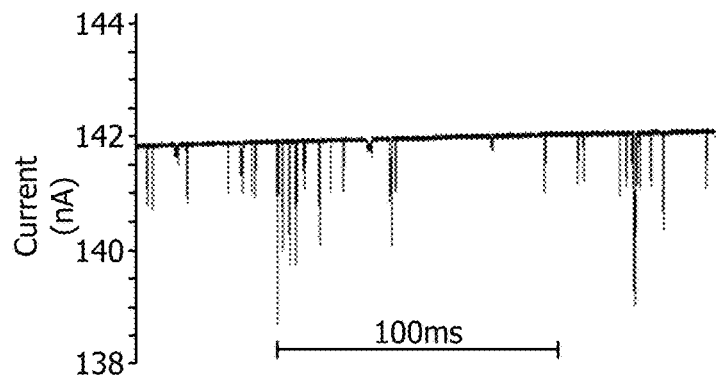
FIG. 2A is a graph of the ionic current versus time for an 870 nm diameter pore at 300 mV with 220, 330, and 410 nm particles in 1 M KCl, ph 8, with 0.1% Tween 80.
Figure 2B:
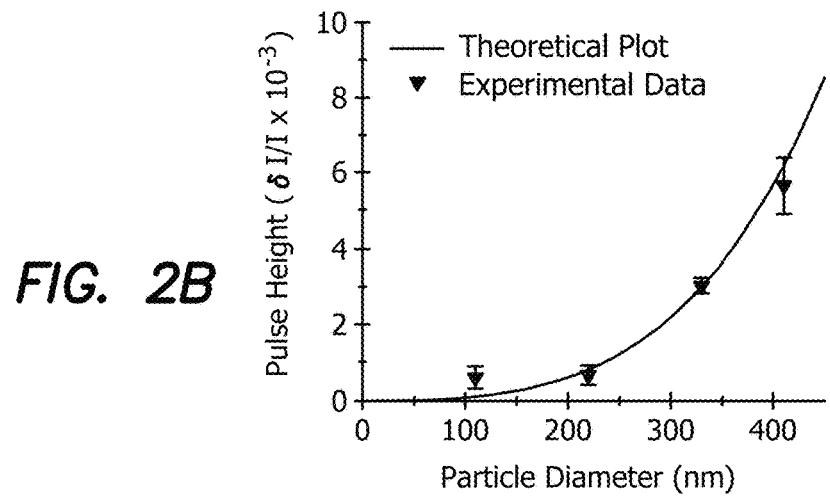
FIGS. 2B and 2C are graphs of event depth versus particle and pore diameter, respectively and their agreement with the predicted values given by equation 1.
Figure 2C:
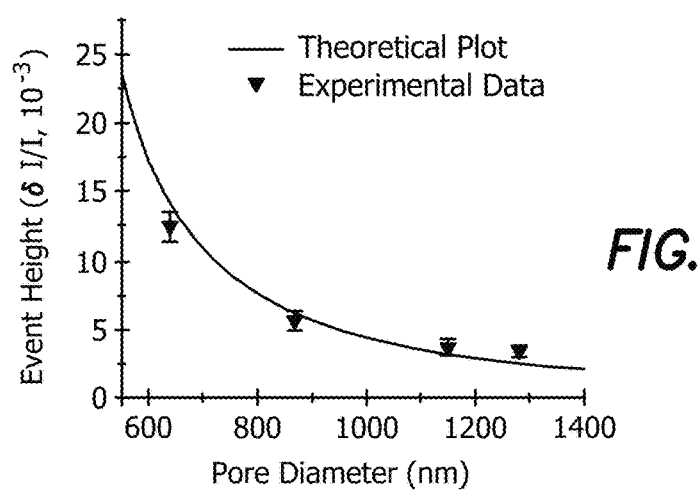

Ionic current versus time for an 870 nm diameter pore at 300 mV with 220 nm, 330 nm, and 410 nm particles suspended in 1M KCl solution with a pH 8 and with 0.1% Tween 80 is seen in FIG. 2A. The carboxyl-functionalized polystyrene particles were electrophoretically driven through the approximately cylindrical 870 nm diameter track-etched pore in a PET membrane, resulting in a transient drop, or "event", in the ionic current as each particle passed through. FIG. 2A shows the ionic current along a time scale, where it can be seen that the event depths are clustered around specific levels. It has been shown in the past that the depth is a function of particle volume and pore geometry and for particles whose size is comparable to the pore diameter the event depth follows the relation of equation 1 and is shown in FIGS. 2B and 2C.

$$\frac{R_{particle} - R_{empty}}{R_{empty}} = \frac{D}{L}\left[\frac{\sin^{-1}\left(\frac{d}{D}\right)}{\sqrt{1-\left(\frac{d}{D}\right)^2}} - \frac{d}{D}\right] \quad (1)$$

$$= \frac{I_{empty} - I_{particle}}{I_{particle}}$$

Figure 17:
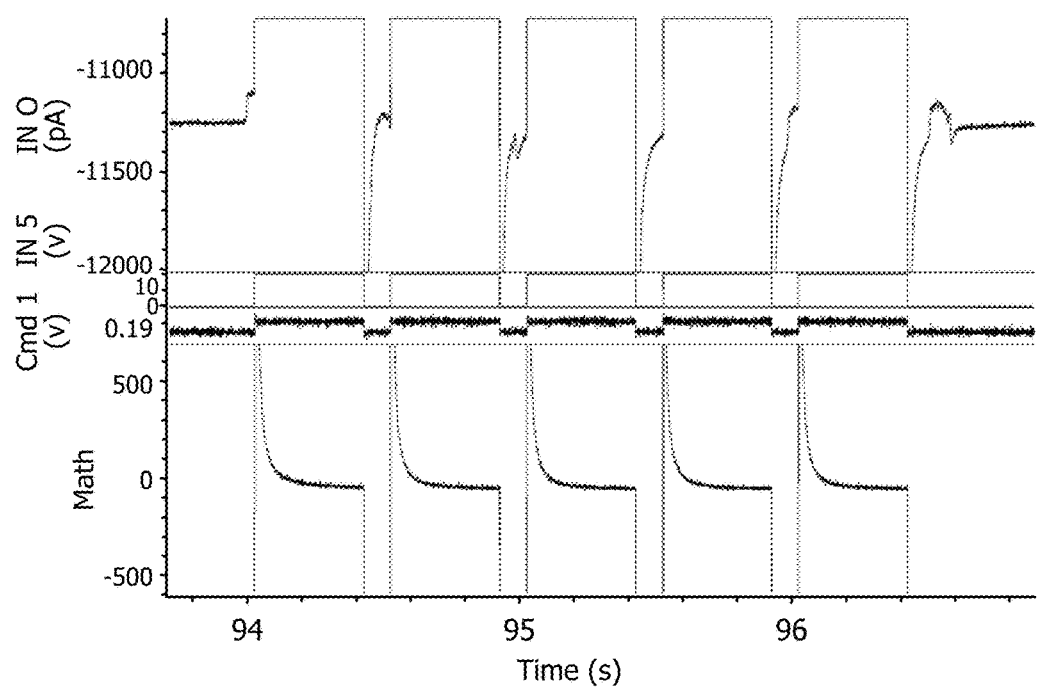
FIG. 17 is a graphical representation of the ion current pulse produced when a single polystyrene 410 nm in diameter particle was trapped in a pore by switching off the driving electric field.

Here, d is the particle diameter, D is the pore diameter, L is the pore length, $R_{particle}$ and $R_{empty}$ are the electrical resistance with and without a particle, and $I_{particle}$ and $I_{empty}$ are the equivalent currents. The pore diameter D was estimated from conductivity measurements assuming cylindrical pore geometry. The value $I_{particle}$ was calculated as an average current blockage in time within each event with respect to the baseline current in the vicinity of that event. Fitting the data shown in FIG. 2B using a different approach that relates the event depth with minimum pore diameter as found from the maximum blockage within each event gave similar results. The concentration of each particle size was $2 \times 10^9$ particles/ml. Note that the slow variation in the baseline was simply a consequence of variations in laboratory temperature occurring on the minutes time scale. FIG. 17 shows where a single polystyrene 410 nm in diameter particle was trapped in a pore by switching off the driving electric field. Due to hindered diffusion in the confined geometry, the particle could stay in the same location for a number of seconds.

Figure 3A:
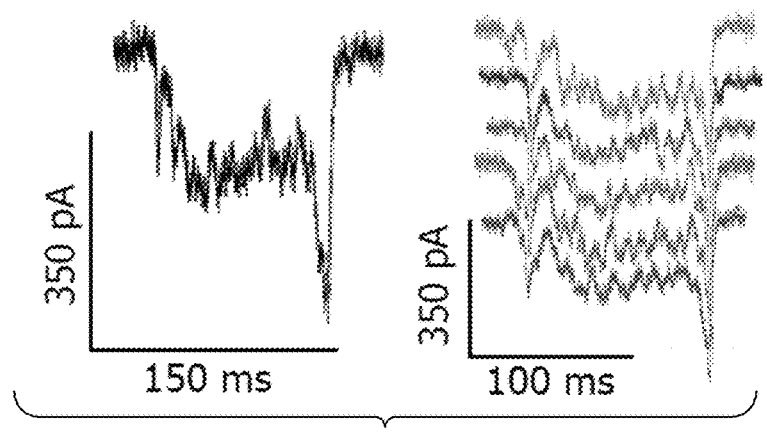
FIGS. 3A-3C are magnified views of ionic current events shown in FIG. 2A for 220, 330, and 410 nm particles, respectively, showing that the events have a characteristic pattern variation irrespective of pore size.
Figure 3B:
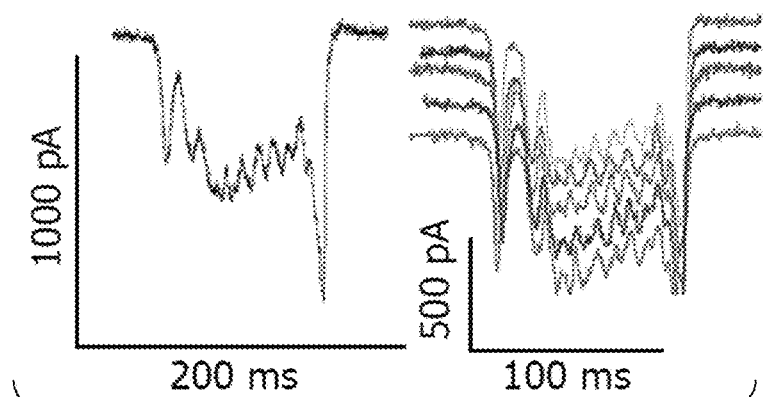
Figure 3C:
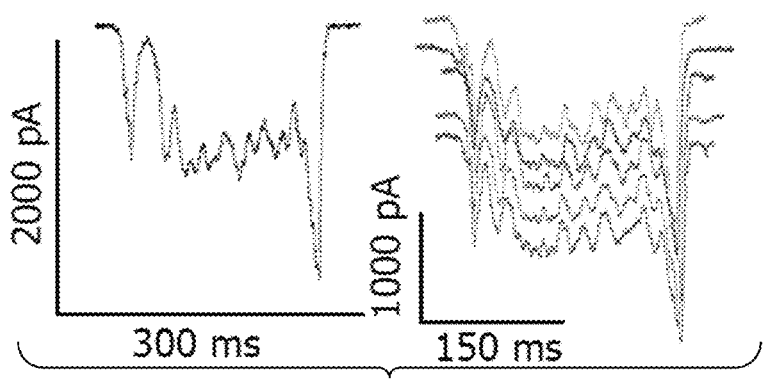
Figure 3D:
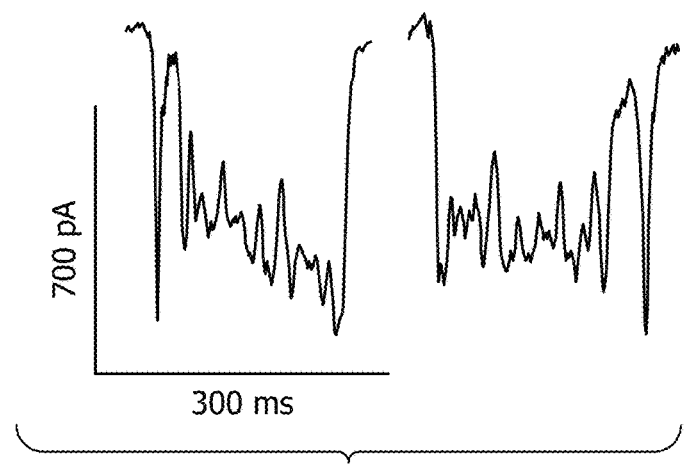
FIG. 3D is a graph of the ionic current versus time for 330 nm particles passing in opposite directions from that of FIGS. 3A-3C through a pore of diameter 520 nm showing that the pattern of variations are reversed for the opposite particle direction.

FIGS. 3A-3C depict magnified views of the ionic current events from FIG. 2A for 220, 330 and 410 nm particles, respectively, showing that the events have characteristic pattern variations irrespective of pore size. A single event is shown on the left, while the right shows five events, vertically offset, highlighting the reproducibility of this characteristic pattern for each particle size. The left side of FIGS. 3A-3C show large variations in current, and these variations occur in a specific pattern that is maintained for all events. This is highlighted on the right side of FIGS. 3A-3C, which presents several events vertically offset to facilitate comparison. Similar, albeit smaller, fluctuations have been observed and it has been proposed that they were due to variations in the pore diameter along its length. We found that the pattern of fluctuations is maintained for different particle sizes seen in FIGS. 3A-3c for 220, 330, and 410 nm particles, respectively. In addition, passing the particles in opposite directions through a pore of a different diameter, the results of which are shown in FIG. 3D, an approach used before when translocating particles through glass pipettes, shows that the pattern of fluctuations is reversed. Note that the left event shows an increasing trend apart from the final dip, which was observed only for particles passing in this direction. As would be expected, the pattern of fluctuations is unique to a particular pore, as can be seen by comparing FIGS. 3A-3C with FIG. 3D.

For a specific pore, the structure of ion current events observed with particles of different sizes is very similar as seen FIGS. 3A-3C. However, the ion current modulations are more pronounced for larger particles, since they obstruct more of the ions flowing through the pore. Although smaller particles can probe the pore with higher spatial resolution (similar to tips in atomic force microscopy), the reduced signal-to-noise ratio creates a trade-off. We note, however, that the particle size does not set a limit on the spatial resolution, as improved results can be achieved by deconvolution. The ultimate limits are the measurement bandwidth, noise, and the deviations in the particle shape from a perfect sphere. By analyzing the optimal particle size versus pore diameter and studying the duration and amplitude of the subpeaks within the ion current events, this will allow us to map the velocity variations as a particle passes through the pore and relate these to local variations in the electric field in the pore.

Figure 3E:
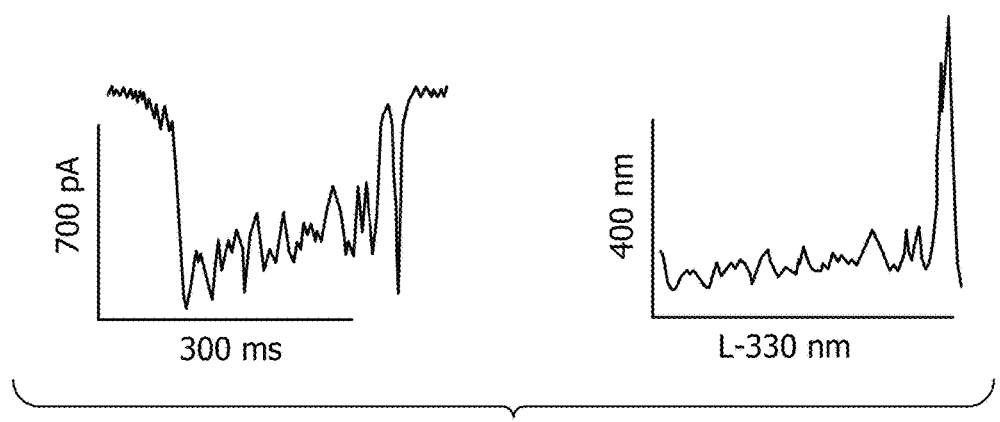
FIG. 3E is a graph of the ionic current versus time for a single 330 nm particle passing through a 520 nm diameter pore together with the pore diameter profile according to the formula given in equation 2.

Finally, SEM images of metal replicas of pores etched under the same conditions show significant variations in diameter along the pore length as seen in FIG. 1 which confirms the hypothesis that the current modulations reflect the varying pore diameter along its axis. In PET pores etched under somewhat different conditions, diameter variations have been attributed to the laminar nature of the film, such that the etchant can penetrate deeper at the interfaces between the strata. We estimated the variations in pore diameter using the first component in equation 2, and an example of which is plotted in FIG. 3E. Note that this is only accurate in the radial direction, as the particle velocity is unlikely to be constant as it moves through the pore.

$$\Delta R = \frac{8\rho d^3}{3\pi D^4}\left[1 + \frac{4}{5}\left(\frac{d}{D}\right)^2 + \frac{24}{35}\left(\frac{d}{D}\right)^4 + \ldots\right] \quad (2)$$

Where ρ in equation 2 represents solution resistivity.

Figure 4A:
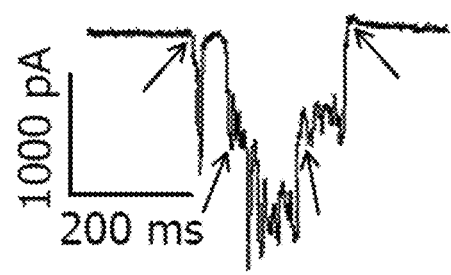
FIG. 4A is a graph of the ionic current versus time for two particles 330 nm in diameter passing through a pore simultaneously.
Figure 4B:
FIG. 4B is a graph of the ionic current versus time for particles temporarily sticking in the pore.

FIG. 4A depicts two particles passing through a pore simultaneously. Note that the ionic current variations enable the motion of each particle to be resolved independently. The arrows in FIG. 4A indicate the entry and exit of each particle. This characteristic pattern of ionic current variations as each particle translocates reveals details about particle motion within the pore. Resolving multiple particles within the pore at the same time, a traditional problem for Coulter counting, becomes straightforward because the instances of the pattern corresponding to each particle can easily be recognized, as shown in FIG. 4A. This is of practical importance, since higher analyte concentrations can be used to provide faster results. Currently, the concentration must be set low enough that multiple particle events are statistically improbable. In addition, it is possible to clearly identify when particles get stuck within the pore, which is indicated by a pause in the characteristic pattern as seen in FIG. 4B. The duration and position of this pause reveal how long the particle is stuck and the point where that happens. For example, the current event shown in the right panel of FIG. 4B indicates that the particle got stuck in the beginning of the translocation process. Finally, the characteristic pattern allows us to determine if particles always completely translocate through the pore, rather than, for example, enter, partially translocate, and exit back out on the same side. In our experiments, particles always translocated completely through the pore. In addition, if individual particles enter and exit the pore multiple times, the occurrence of translocation events in time would not follow a Poissonian distribution. As expected, our data are Poissonian.

In both FIGS. 4A and 4B, the particles were 330 nm in diameter in 1 M KCl, pH 8 with 0.1% Tween 80. The same 520 nm mean diameter pore as in FIG. 3D was used, and the applied voltage was 300 mV.

Figure 5A:
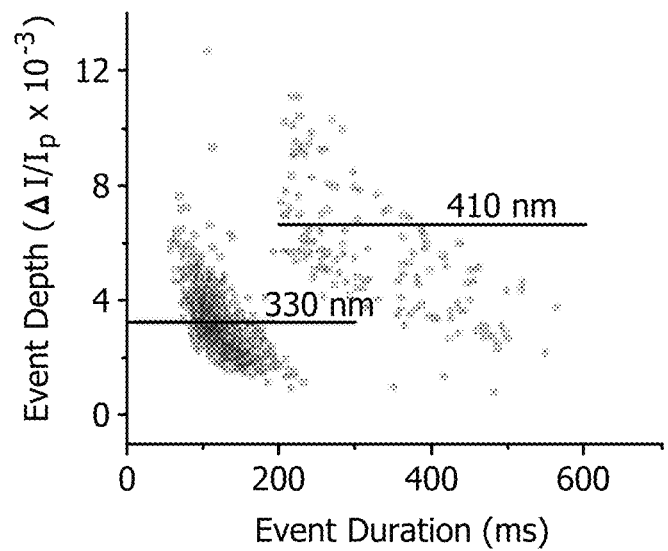
FIG. 5A is a scatter plot of event depth versus duration for a mixture of 330 and 410 nm particles.
Figure 5B:
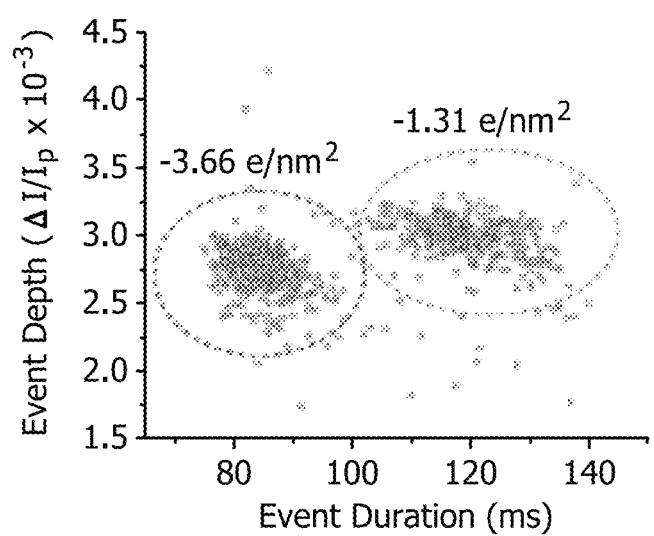
FIG. 5B is a scatter plot of event depth versus duration for a mixture of two types of 410 nm particles with fully ionized surface charge densities of −1.31 and −3.66 $e/nm^2$.

As has been done in the past, we demonstrate discrimination between particles of different sizes. FIG. 5A shows a scatter plot of event depth versus duration for a mixture of 330 and 410 nm particles passing through an 870 nm pore. It is evident that the events are clustered according to their size, so that they can be discriminated in a mixture. As discussed earlier, the particle volume can be computed from the event depth and pore geometry. FIG. 5A also highlights that events differ, not only in depth, but also in duration. It has been shown that event duration depends on the effective charge of the particle, in tandem with hydrodynamic drag. Following that work, we explored charge sensitivity by studying a mixture of 410 nm carboxyl-functionalized polystyrene particles, differing only in surface charge. FIG. 5B plots event depth versus duration for this experiment and shows that the particle types can be clearly distinguished based on event duration, even though there is negligible difference in event depth (the sizes calculated from the mean depths are within the distribution of sizes measured using a Zetasizer, Nano ZS, Malvern Instruments, Ltd.).

Figure 6A:
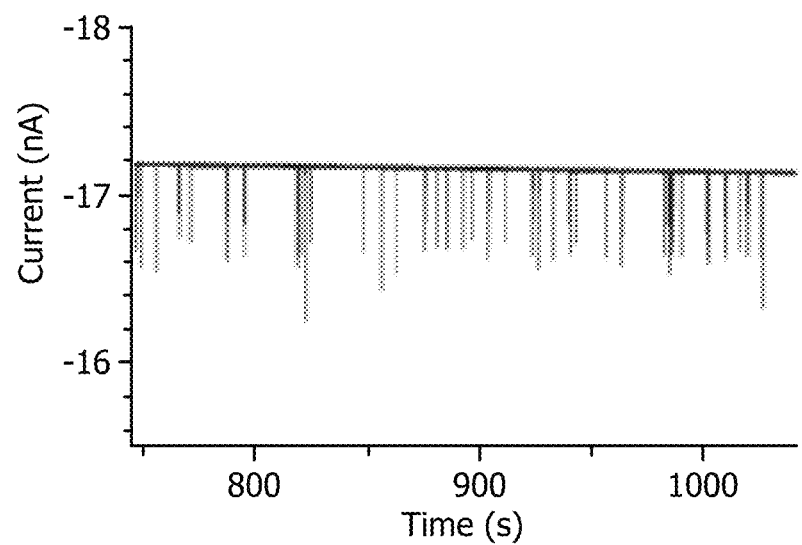
FIGS. 6A and 6B are graphs of current versus time when electroosmotic flow is used to transport particles through a pore and when electroosmotic flow is eliminated, respectively.
Figure 6B:
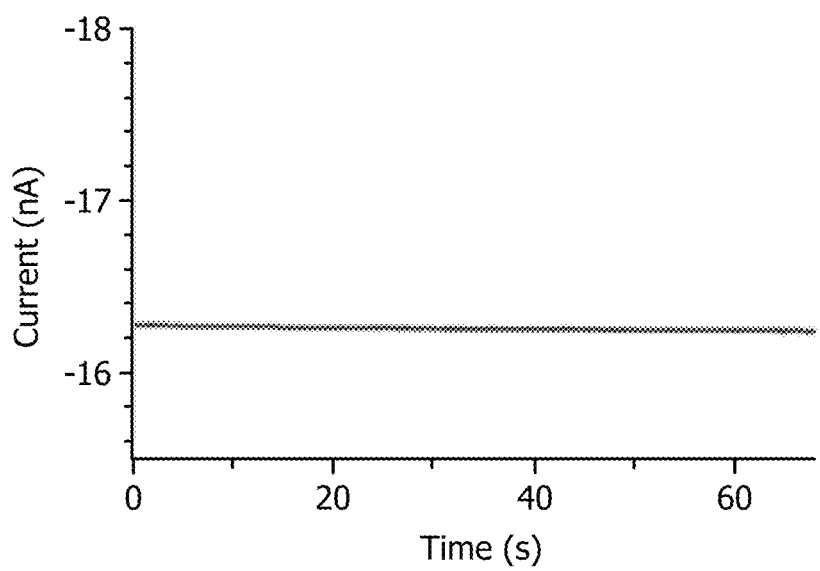

Track-etched PET pores are known to have —COOH surface groups that are negatively charged at basic pH which is likely to induce electroosmotic flow, as demonstrated recently in other nanopore systems. To confirm this, we carried out experiments with uncharged poly(methylmethacrylate) (PMMA) particles, which should not experience electrophoresis. At pH 3, when the surface groups are fully protonated, and thus there should be no electroosmotic flow, we do not observe any particle translocations as seen in FIG. 6B. However, at pH 10, when the surface groups should be completely ionized, particles are observed translocating through the pore toward the cathode, which is the direction of electroosmotic flow as seen in FIG. 6A. The lack of translocations observed in the electrophoretic direction (positive voltages) confirms that the PMMA particles used in the experiments were indeed uncharged, indicating that no significant hydrolysis of the ester bonds occurred at pH 10. Thus, in our experiments with negatively charged particles, electroosmosis opposes particle transport, reducing the velocity compared to electrophoresis alone. The tests for electroosmosis were performed in 0.1 M KCl rather than 1 MKCl to enhance the effect of surface charges on ionic and particle transport.

Figure 16A:
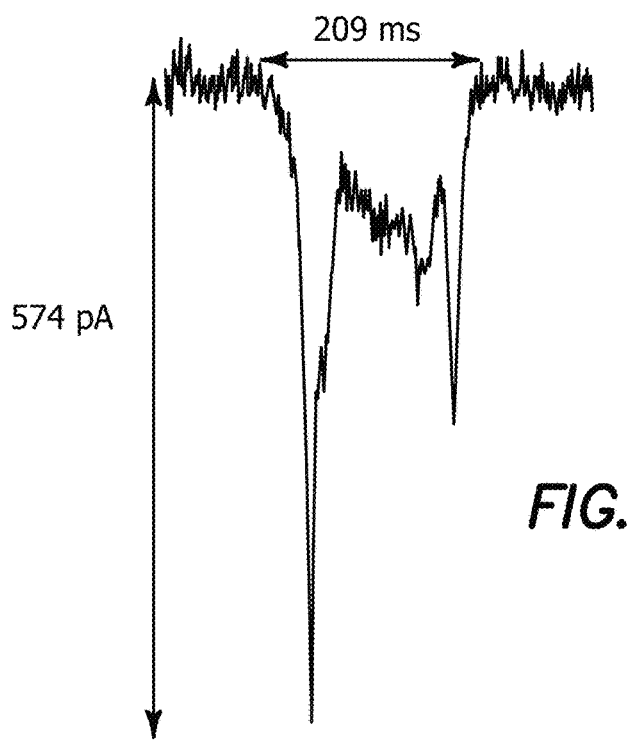
FIG. 16A is a graphical representation of the ion current pulse produced when *Escherichia coli*, which is rod shaped, passes through the pore.
Figure 16B:
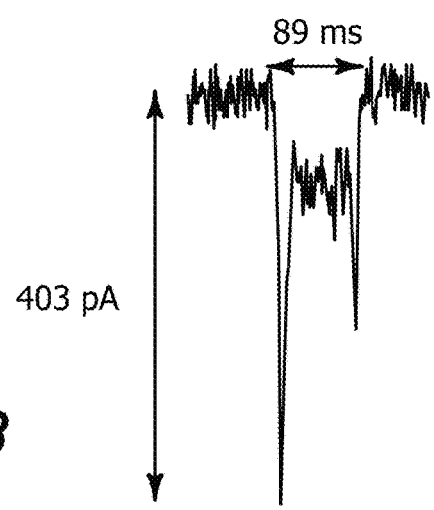
FIG. 16B is a graphical representation of the ion current pulse produced when *Staphylococcus aureus*, a round cell, passes through the pore.

The principles above can be used in a variety of real world applications, for example in the testing for the presence of certain biological cells in a given sample of fluid. *Escherichia coli* bacterial cells passing through a single pore with an opening diameter of 5.5 micrometers is shown in FIG. 16A. Furthermore the ability of the pore to differentiate the shape of cells is demonstrated in FIGS. 16A and 16B. *Escherichia coli*, which is rod shaped, was first passed through the pore, producing ion current pulses as exemplified in FIG. 16A. The pore was then cleaned and subsequently *Staphylococcus aureus*, a round cell of a similar volume to *Escherichia coli*, was passed through the pore. Shape of resistive pulses produced by *Staphylococcus aureus* is shown in FIG. 16B. Amplitude and shape of resistive pulses produced by the two types of cells are indeed different. These experiments were performed in a solution of 0.3 KCl at pH 7.4.

Figure 7A:
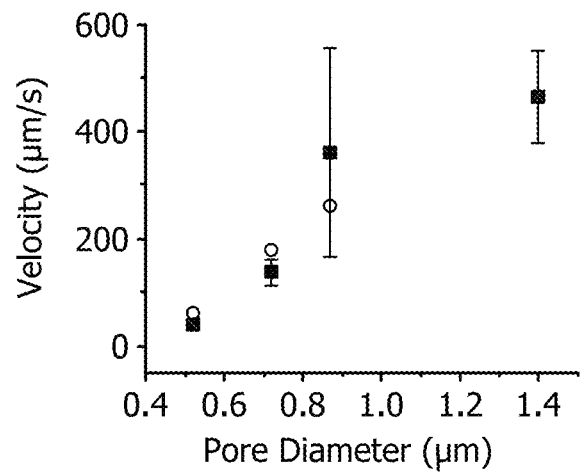
FIG. 7A is a graph of measured velocity versus pore diameter compared to velocities calculated from the reduction factors with respect to the velocity for the largest pore.
Figure 7B:
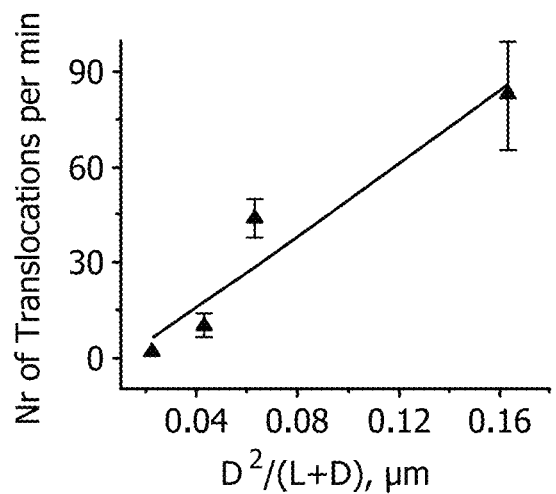
FIG. 7B is a graph of the measured number of translocations per minute versus pore diameter.
Figure 8A:
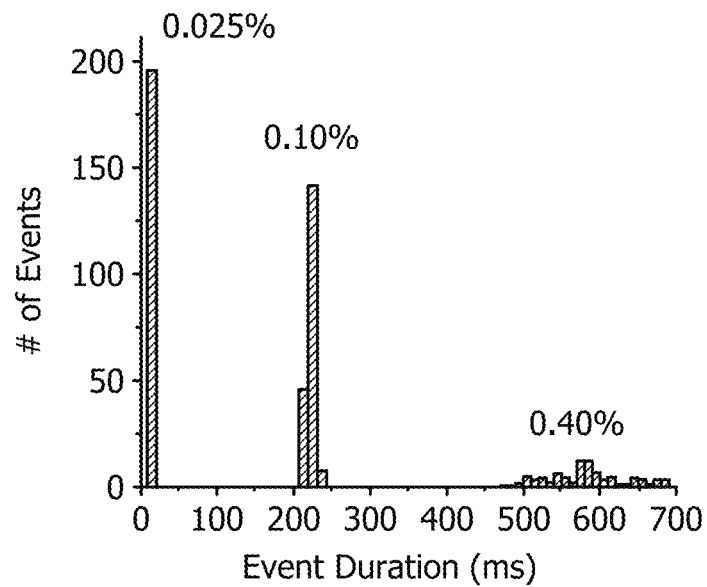
FIG. 8A is a bar graph of the number of events versus event duration on the influence of Tween 80 surfactant concentration on the velocity of 410 nm particles passing through a 1360 nm mean diameter pore.
Figure 8B:
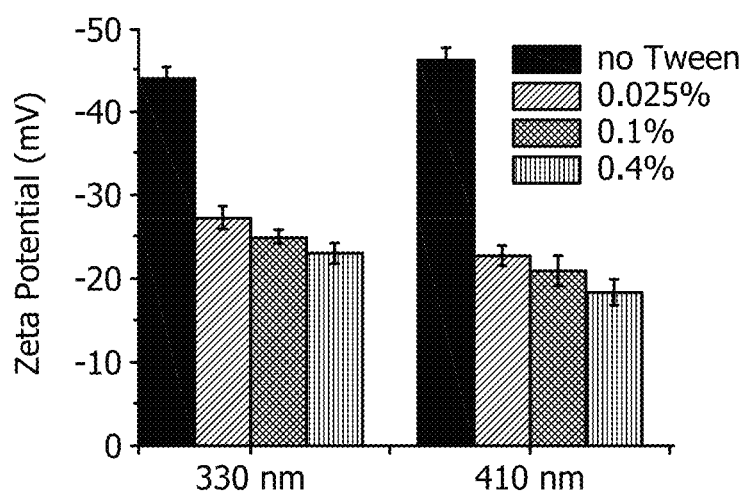
FIG. 8B is a bar graph of the measured Zeta potential for 330 nm and 410 nm particles measured in a range of surfactant concentrations.

FIG. 7A plots the velocity of 330 nm particles through pores of a range of sizes. It can be seen that the velocity increases by over an order of magnitude as the mean pore diameter increases from 520 to 1400 nm. In a narrow pore, the proximity of the walls will introduce hydrodynamic drag, slowing particle translocation. We find that the corresponding velocity reduction factors previously known with respect to the velocity in a 1400 nm in diameter pore accurately describe our data seen in FIG. 7A. In the calculations, only electrophoretic transport was considered. Also, as expected with smaller pores, due to the decreased volume in which particles can be captured by the electric field, the event rate also decreases with pore size as demonstrated in FIG. 7B. According to previous known modeling, the rate of collisions of particles with the pore opening scales with the pore diameter as $D^2/(L+D)$ if the applied voltage assures that each nanoparticle arriving at the pore mouth will translocate the pore. Our data are indeed in agreement with the model as seen in FIG. 7B. Although surfactant is routinely added in resistive-pulse sensing, to avoid particles sticking to each other or the pore, the effect of that surfactant on particle motion has been little explored. It has been noted that uncharged particles behave as if they have an effective positive charge when using the nonionic surfactant Triton X-100. With the same surfactant, they also observed that the effective charge of carboxyl-modified polystyrene particles was significantly lower than the number of ionizable —COOH functional groups. We show that the event duration, and thus mean particle velocity, depends very significantly on the concentration of surfactant (in the current case Tween 80). FIG. 8A shows that for an approximately 20-fold increase in Tween 80 concentration the particle velocity decreases by a similar factor. Note that changes in the solution viscosity are not responsible, as it remains the same. Our reasoning for this correlation follows the hypothesis proposed by Sun and Crooks (Sun, L.; Crooks, R. M. Single Carbon Nanotube Membranes: A Well-Defined Model for Studying Mass Transport Through Nanoporous Materials. *J. Am. Chem. Soc.* 2000, 122, 12340-12345) that crown-ether-like interactions between $K^+$ ions and particle-bound Tween 80 molecules bind $K^+$ ions to the particle, making its effective charge more positive. To support this hypothesis, we measured the zeta potential of these particles in various surfactant concentrations as seen in FIG. 8B. For a fixed particle size and electrolyte concentration, surface charge is proportional to zeta potential which indicates that the effective particle charge does decrease with increasing surfactant concentration. Note that the instrument used was not capable of measuring zeta potential with the 1 M KCl concentration used in many of our resistive-pulse sensing experiments, due to its high conductivity. As would be expected, since the particles have more time to diffuse at lower velocity, the distributions of translocation times are broader for higher surfactant concentration.

In addition to using resistive-pulse sensing to map the physical variations of the structure of a pore, it may also be used to detect the deformation of hydrogel particles and any other deformable object as they pass through the pore and the related formation of depletion zones which may be used during the transportation of biological cells. FIGS. 9A and 9B compares the passage of two types of particles, 220 nm diameter carboxyl-modified polystyrene beads and approximately 300 nm diameter hydrogels respectively, through a 12 µm long track-etched PET pore with an average opening diameter of 540 nm. The size of all particles was measured using a Zeta sizer Nano ZS (Malvern Instruments, Westborough, Mass.) as a function of ionic strength. The size of the polystyrene beads (220 nm) was found to be independent of the salt concentration. The diameter of the hydrogels was measured with 5% precision to be 320 nm, 300 nm, and 260 nm in 1 mM, 10 mM, and 0.1 M KCl, respectively. All KCl solutions were buffered to pH 10 with 10 mM Tris and contained 0.01% by volume Tween 80. At pH 10 the hydrogel particles are negatively charged and swollen due to the deprotonation of carboxyl groups in the hydrogel network.

The polystyrene particles are a model system for hard spheres; thus, these particles do not deform in the pore. As expected, passage of the beads causes a transient decrease of the transmembrane ion current, called a resistive pulse, corresponding to a transient pore obstruction. The shape of the resistive pulses can also reflect the undulating pore diameter along the pore axis, as previously reported for PET pores. The polystyrene particles therefore play a role of an internal probe of the pore topography. According to the shape of the resistive pulses, we predict that the pore shown in FIGS. 9 and 11 contains a larger cavity in the middle flanked by narrower regions of the pore. The presence of a brief current increase after each particle exits the pore was a subject of our most recent studies (J. Menestrina, C. Yang, M. Schiel, I. V Vlassiouk, Z S. Siwy, Charged Particles Modulate Local Ionic Concentrations and Cause Formation of Positive Peaks in Resistive-Pulse Based Detection, *J Phys. Chem. C* 2014, vol. 118, pp. 2391-2398). We assume ion current modulations within a resistive pulse are indeed indicative of the undulating pore opening. Transport of polystyrene particles occurred by electrophoresis, where the negatively charged particles moved toward a positively biased electrode.

Hydrogel particles are characterized by a lower value of the zeta potential (−24±8.0 mV) compared to the polystyrene beads (−47±9.0 mV), and the hydrogels were able to pass through the same pore only by electroosmosis. The particles, although negatively charged, moved toward the negatively biased electrode. Due to the negative charges as well as the branched, low-density structure of the hydrogels, the number of cations that the particles introduced into the pore was in fact higher than the number of ions that were displaced. In other words, the hydrogel conductance in 100 mM KCl (and in 10 mM KCl as discussed further below) is higher than the conductance of the bulk solution. As a result, the presence of the particles at the pore entrance and in the pore caused a decrease of resistance of the particle/pore system, leading to a higher value of the current compared to the baseline. The shape of the current pulses was similar to the one obtained with the polystyrene particles, except instead of a current decrease, a current increase was seen as demonstrated in FIG. 10. The features of the resistive pulses with hydrogels were often better resolved at higher voltages compared to the experiments performed with hard spheres, because the current increase had a relatively small amplitude; thus higher voltages improved the signal-to-noise ratio. In FIG. 10, comparison of non-deformable hard spheres (polystyrene particles shown on left) and soft (squishy) hydrogels (shown in the right panel) are shown passing through the same 540 nm diameter pore. The current decrease at the end of the translocation process of the hydrogels seen in the right panel was attributed to the deformation of the hydrogel as well as formation of a depletion zone. The time between the entrance of the particle to the pore and when the particle underwent deformation observed as the maximum current decrease can be used as a measure of the particle's ability to deform, and is expected to be correlated with the particle Young modulus. Particle deformation is also expected to be determined based on the changes of the sub-peaks of each resistive pulse when compared with experiments performed with hard spheres.

In the course of the particle translocation however, typically at the end of the trajectory, the current gradually decreased to a level below the background current. A similar shape of the current events, i.e., current increase followed by a decrease, was observed before in the experiments of pressure-driven passage of deformable microgels through glass pipettes. The current decrease occurred only in previous experiments in which the pipet diameter was smaller than the particle size and was explained as a combination of particle deformation and dehydration. Observation of the current decrease with 300 nm particles passing through a 540 nm diameter pore was unexpected.

In some cases, 2 out of 15, the current decrease occurred in the middle of the translocation process rather than at the end of the particle trajectory. The location of the particle could be determined since only part of the pore structure seen with polystyrene particles was observed in the pulses of the hydrogels.

In order to determine which processes were responsible for the current increase and decrease seen during hydrogel translocations, similar experiments to those shown in FIG. 9 were performed with pores of different opening diameters between 200 and 1600 nm. The pore with an average diameter of 330 nm was the smallest structure through which the hydrogel passage was observed. In all experiments, hydrogel transport occurred only by electroosmosis; no electrophoretic translocations of hydrogels were recorded. The shape of the current changes was qualitatively the same for all pores (i.e., a current increase followed by a decrease below the baseline value), independent of their diameter.

Figure 11:
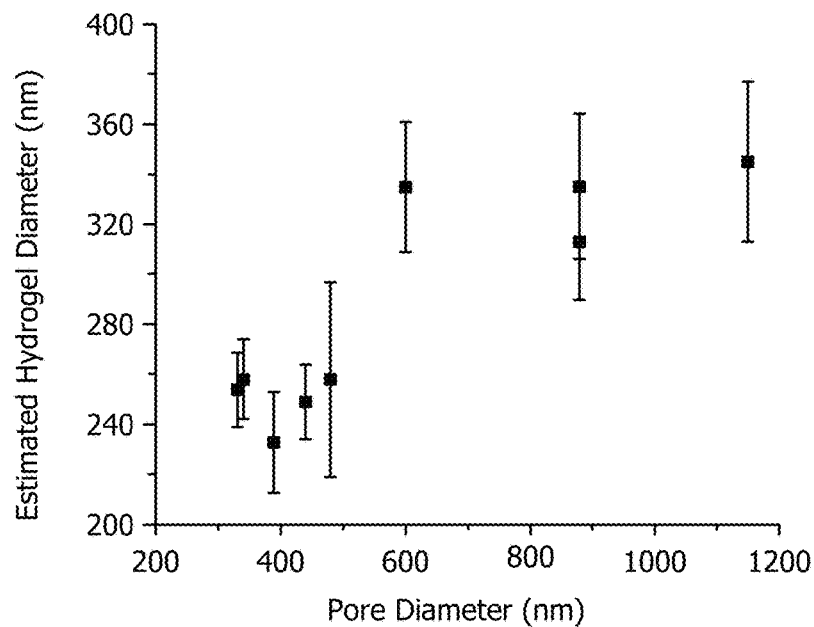
FIG. 11 is a graph of the size of the hydrogels as a function of the pore diameter.

The resistive pulses were first analyzed by the amplitude of the current decrease, which is a measure of the particle size if we assume that the particle underwent a complete dehydration and deionization. Compression of the particles would decrease their volume and conductivity; thus the effective size would correspond to a sphere smaller than the original particle size. FIG. 11 presents an average effective particle diameter as found from resistive pulses (the lowest recorded current) obtained with 300 nm hydrogels passing through pores with various opening diameters. The smaller effective diameter of the particle in pores with openings between 300 and 450 nm suggests that when translocating the hydrogels underwent both processes of deformation and dehydration.

The hydrogel dehydration and deformation was observed before only in pressure-driven experiments; therefore we asked the question whether electroosmotic flow through our pores could potentially result in an inhomogeneous pressure distribution along the pore axis. The modeling was performed by numerically solving the coupled Poisson-Nernst-Planck (PNP) and Navier-Stokes (NS) equations (Comsol Multiphysics), as reported before. Two types of structures were considered: a smooth cylindrically shaped pore and a pore containing a wider cavity in the middle. The existence of such cavities was confirmed by preparing a metal replica of pores in PET. The calculations required rather extensive computational power, because to ensure convergence of the solutions, the mesh size close to the charged walls had to be reduced to 0.1 nm. The maximum length of the modeled pores was therefore 1.5 μm (versus 12 μm length of the pores used in the experiments) to make solving PNP and NS equations in 3D possible. In order to understand dependence of the solution on the pore length, the modeling was performed for three different values of pore length between 600 nm and 1.5 μm.

The obtained pressure (with respect to atmospheric pressure) along the axis of two 1.5 μm long pores that carry surface charge of $-0.25$ e/nm$^2$ with different geometries is shown in FIG. 12, where the direction of electroosmotic flow will be from $+1$ to 0 V, or from right to left. Due to undulating current amplitude within a resistive pulse seen in FIG. 10, the structure shown in FIG. 12B is a better representation of our experimental system. Results for two cylindrically shaped pores with an opening diameter of 350, and 550 nm are shown in FIG. 12A. A pore with undulating pore diameter between 350 nm and 550 nm is shown in FIG. 12B. The KCl bulk concentration was 10 mM. Pressure values with respect to the atmospheric pressure of 1 atm are shown.

We interpret the results in the following way. The local negative pressure at the pore entrance can facilitate the particle translocation. Toward the pore exit, the local pressure is positive, which we think could play an important role in the particle deformation and dehydration. The absolute values of the pressure were substantially affected by the presence of the wider cavity, and the change in the pressure from negative to positive occurred over a smaller distance in the structure with varying pore diameter.

The developed pressure profile results from the electroosmotic fluid flow, which in turn depends on the electric field across the pore. It was important therefore to understand the dependence of the pressure distribution on the pore length. FIG. 13A presents numerical calculations of pressure along a pore axis for cylindrical pores with an opening diameter of 350 nm and lengths of 600 nm, 900 nm, and 1.5 μm. A voltage of 1 V was applied across all structures. The pressure profile was qualitatively the same for all pores; however the maximum value of positive pressure decreased with the increase of the pore length. The positive pressure in 12 μm long structures used in the experiments is therefore expected to be lower than the calculated values.

In contrast to the results for cylindrical pores, structures with an undulating pore diameter showed very little dependence of the maximum magnitude of the positive pressure on the pore length as seen in FIG. 13B. We think the pressure profile in this case is dominated by the boundary between the pore regions with two different opening diameters and to a lesser extent by the total pore length. It is possible therefore that even a 12 μm long pore has pressure values along the axis comparable to those found numerically for much shorter pores.

Two zones of negative and positive pressure, respectively, were predicted before to occur in a nanofluidicionic transistor in which two regions of the channel walls with negative surface charges were separated by a neutral region or a positively charged region. We hypothesize that our pores with an undulating pore diameter could be equivalent to such systems with inhomogeneous surface charges with lower effective surface charge density at the regions with wider openings.

According to the model predictions, the values of the developed electroosmotic pressure are a function of the pore diameter and diminish for wider pores as seen in FIG. 12A. As a result, no significant particle dehydration or deformation is expected to occur in pores with an opening diameter greater than 450 nm as demonstrated in FIG. 11. The shape of the resistive pulses caused by hydrogel particles was however independent of the pore diameter. Moreover, the magnitude of the current decrease in wider pores was equivalent to a particle larger than the studied 300 nm diameter hydrogels in FIG. 11. On the basis of these observations we concluded that the current decrease in wider pores is caused by a different phenomenon than deformation or dehydration.

In order to explain the shape of resistive pulses in pores with large opening diameters, we calculated the concentration of ions in the hydrogel particles and compared the values to the bulk concentration in Table 1 below.

TABLE 1

TABLE 1. Calculations of Ionic Molarity in Hydrogel Particles Based on Integrating Positive Peaks in Resistive Pulses Obtained in Pores of Different Diameters$^a$

| pore diameter, bulk concentration | molarity in the particle |
| --- | --- |
| 330 nm, 0.01M | 0.11 ± 0.02M |
| 390 nm, 0.01M | 0.11 ± 0.03M |
| 440 nm, 0.01M | 0.06 ± 0.02M |
| 660 nm, 0.01M | 0.25 ± 0.06M |
| 500 nm, 0.1M | 1.03 ± 0.81M |
| 540 nm, 0.1M | 0.82 ± 0.24M |

The calculations were performed on the basis of the positive peak of the resistive pulses, which carry information on the number of additional ions that each particle brings to the pore, and the hydrogel size as found from the dynamic light scattering measurements. The hydrogel detection was carried out in 10 mM KCl and 0.1 M KCl. Nearly for all experiments, the ionic concentration in the particle was 10 times higher than in the bulk. The similarity of these values is likely due to osmotic pressure equilibrium, with the ratio between the particle and the bulk remaining similar regardless of the bulk ionic concentration.

Figure 14A:
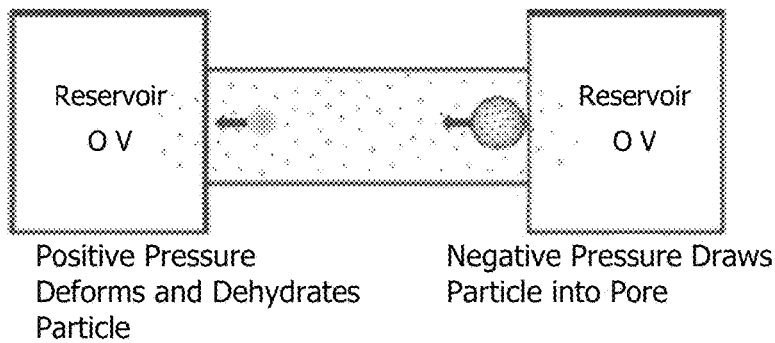
FIGS. 14A and 14B are schematic diagrams of electroosmotic passage of hydrogels through pores with openings less than 450 nm, and in wider pores with openings greater than 450 nm, respectively.
Figure 14B:
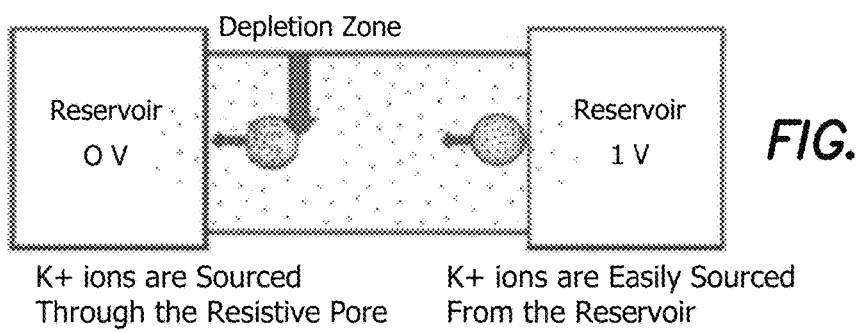

The large difference in ionic concentrations in the particle and in the bulk as well as higher mobility of ions versus the particle's mobility set the stage for the concentration polarization. Since the hydrogels are moving in the same direction as potassium ions, there will be an ionic depletion at the back of the particle and ionic concentration enhancement in front of the translocating particle as seen in FIG. 14B. Concentration polarization was observed before in the vicinity of hydrogel plugs immobilized inside a microchannel. In our case, the hydrogel is moving; thus we can conclude that the formation of the depletion zone is faster than the translocation velocity of the hydrogel.

Formation of the depletion zone would also explain why the current decrease occurred only toward the end of the particle passage through a pore. When the particle is close to the pore entrance, the influx of potassium ions to the particle is unhindered as seen in FIG. 14B. When the particle is moving along the pore axis and reaches the pore exit, the potassium ions have to be provided through the whole length of the pore, which plays a role of a resistive element. As a result, the concentration polarization becomes more pronounced once the particle reaches the opposite end of the pore.

The ion current decrease that we observe for pores with diameters larger than 450 nm is therefore a measure of the size of the depletion zone, which limits the ionic transport. We found the depletion zone diameter (assuming it is spherical in shape) is independent of the pore size in FIG. 11 and applied voltage in the studied range of up to 2 V. It is also interesting that the depletion zone is larger than the translocating hydrogel particles. This observation is in agreement with earlier studies of concentration polarization showing the depletion zone can extend over large distances.

In order to provide additional evidence for the universal shape of resistive pulses obtained with hydrogels, we performed experiments with negatively charged pores in another polymer material, polycarbonate. The hydrogel particles passed through polycarbonate pores by electroosmosis as well, producing similarly shaped resistive pulses to those obtained with PET pores in FIG. 14.

Figure 15A:
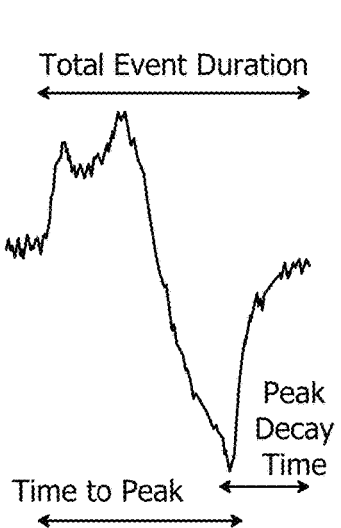
FIG. 15A is graphical representation of a resistive pulse duration.

As the next step, we analyzed how the pore diameter influences the pulse duration, which is a measure of the particle velocity in the pore. In the case of hard spheres we observed an increase of the translocation time with a decrease of the pore diameter. This is because particles experience an additional drag force stemming from the tight fit between the particle and the pore walls. The shape of the resistive pulses observed with hydrogels was more complex. To characterize their duration, three times were considered: (i) the time from the beginning of the pulse to the lowest current, (ii) the time from the lowest current value until it reaches the baseline current, and (iii) the total duration of the event, which is the sum of times (i) and (ii) shown in FIG. 15A.

In general, the dependence of the translocation times of hydrogels on pore diameter does not follow a simple relationship. We believe this stems from the interplay between two phenomena, particle deformation and building up of a depletion zone, whose influence on the particle translocation is most probably dependent on the pore diameter. Our earlier analysis based on the magnitude of the current decrease in FIGS. 11 and 14 suggests that passage of hydrogels through narrow pores is dominated by the particle deformation; transport of the particles through wider pores leads to the formation of a depletion zone. The presented measurements however do not allow us to determine to what extent each of the two phenomena can affect hydrogel transport in a pore of a given diameter.

Figure 15B:
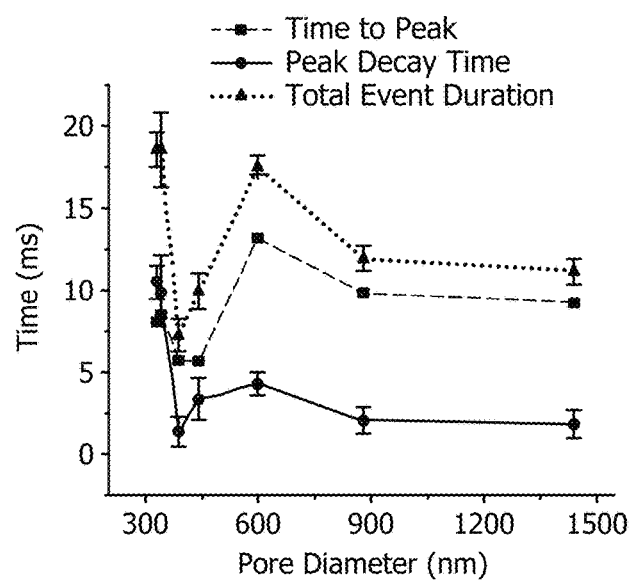
FIG. 15B is a graph of time versus pore diameter for three resistive pulses obtained with hydrogels translocating through pores of different diameters.

In spite of the complexity of FIG. 15B, we would like to point to two important observations. Time (i), between the beginning of the pulse to the lowest value of the current, was found extremely reproducible: the black symbols in FIG. 15B are averages of at least 500 pulses, and the error bars are smaller than the plot symbols. We do not yet have an explanation for this. Time (i) was also found to be longer for wider pores. This observation can be explained by taking into account the movement of both the particle and the depletion zone. The transported "object" is now larger than just the particle, and a higher drag force hinders its transport.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A method of resistive-pulse sensing and physical and mechanical characterizing of a plurality of particles in a solution comprising:
   driving the plurality of particles through a pore, the pore comprising a fluctuating diameter along its length;
   monitoring the pattern of the ionic current of at least one of the plurality of particles as it traverses the length of the pore;
   detecting a change in the pattern of the ionic current; and
   analyzing the duration and amplitude of a plurality of subpeaks within the transient change in the pattern of the ionic current,
   wherein detecting the change in the pattern of the ionic current further comprises differentiating the sizes, shapes, mechanical properties, and chemical affinity of the plurality of particles by measuring the duration and amplitude of the transient drop in the pattern of the ionic current.

2. The method of claim 1 where driving the plurality of particles through a pore with a fluctuating diameter along its length comprises driving the plurality of particles through the pore by electrokinesis, pressure gradient, osmosis, or concentration gradient.

3. The method of claim 1 where detecting a transient change in the pattern of the ionic current comprises detecting a pause in the pattern of ionic current corresponding to a transient sticking of at least one particle in the pore, and relating the pause to a specific location along the pore axis.

4. The method of claim 3 where detecting a pause in the pattern of ionic current corresponding to a transient non-specific sticking of at least one particle in the pore further comprises detecting a specific binding place of a recognition agent for an analyte within the solution to the particle.

5. The method of claim 3 where detecting a pause in the pattern of ionic current corresponding to a transient sticking of at least one particle in the pore further comprises detecting a non-specific adsorption of a recognition agent for an analyte disposed on an inner surface of the pore in a known location along the pore axis.

6. The method of claim 3 further comprising mapping fluctuating diameter of the pore using a plurality of detected amplitude changes in the pattern of ionic current.

7. The method of claim 1 where detecting a change in the pattern of the ionic current comprises confirming when an individual particle completely translocates the pore.

8. The method of claim 7 further comprising mapping an undulating diameter of the pore using the ionic current patterns measured from a plurality of particle translocations.

9. The method of claim 1 where analyzing the duration and amplitude of the plurality of subpeaks within the change in the pattern of the ionic current further comprises resolving the independent motion of each of the plurality of particles in the pore.

10. The method of claim 1 where the detecting a change in the pattern of the ionic current corresponds to the deformation of the passing particles and characterization of the particle mechanical properties.

11. The method of claim 10 further comprising measuring the ability of at least one of the plurality of particles to deform by measuring the elapsed time between the at least one particle entering the pore and a measured current change corresponding to the change of the particle size.

12. The method of claim 1 where at least one of the plurality of particles is a biological cell.

13. The method of claim 1 where driving cells through a pore with undulating opening diameter allows for simultaneous characterization of size, shape and mechanical properties of individual cells.

14. The method of claim 1 further comprising stopping at least one of the plurality of particles being driven through the pore by switching off an external pressure and voltage and wherein the at least one particle can be passed through the same pore multiple times without exiting the pore.

15. The method of claim 1 further comprising resolving the physical and mechanical characteristics of a plurality of individual particles that are present within the pore at the same time.

16. The method of claim 1, wherein the pore is larger than a diameter of the at least one of the plurality of particles.

17. The method of claim 1, wherein the pore accommodates at least two of the plurality of particles at the same time.

18. A method for detecting the non-specific or specific adsorption of a recognition agent for an analyte comprising:
disposing the analyte on an inner surface of a pore;
driving a solution comprising a recognition agent for the analyte through the pore;
monitoring the pattern of an ionic current of the recognition agent as it traverses the length of the pore at various combinations of electrokinetic and pressure-difference driven transport properties;
detecting a transient change in a pattern of the ionic current; and
measuring the ability of the passing recognition agent to deform by measuring the elapsed time between the recognition agent entering the pore and a measured maximum current change.

19. The method of claim 18 where a detecting the transient change in the pattern of the ionic current comprises detecting a pause in the pattern of ionic current corresponding to a transient sticking of the recognition agent to the analyte disposed in the pore at a known location along the pore axis.

20. The method of claim 19 where detecting a pause in the pattern of ionic current corresponding to a transient sticking of the recognition agent to the analyte disposed in the pore further comprises detecting a specific binding place of the recognition agent to the analyte disposed in the pore.

21. The method of claim 18 where driving the solution comprising a recognition agent for the analyte through the pore comprises driving the solution through the pore by a combination of electroosmosis, electrophoresis and pressure difference.

22. The method of claim 18 wherein driving the solution comprising a recognition agent for the analyte through the pore comprises driving the solution through a pore, the pore comprising a fluctuating diameter along its length.

\* \* \* \* \*